United States Patent
Klagge et al.

(10) Patent No.: US 8,642,698 B2
(45) Date of Patent: Feb. 4, 2014

(54) COPOLYMERIZABLE (METH)ACRYLIC ACID ESTERS

(75) Inventors: Ronald Klagge, Erkrath (DE); Thomas Schliwka, Bergisch Gladbach (DE); Uwe Held, Velbert (DE); Thomas Mausberg, Haan (DE); Katharina Hömberg, Hilden (DE); Stefan Busch, Düsseldorf (DE); Shailesh C. Shah, Dresher, PA (US)

(73) Assignee: Cognis IP Management GmbH, Duesseldolf (DE)

( * ) Notice: Subject to any disclaimer, the term of this patent is extended or adjusted under 35 U.S.C. 154(b) by 17 days.

(21) Appl. No.: 13/132,638

(22) PCT Filed: Nov. 26, 2009

(86) PCT No.: PCT/EP2009/008416
§ 371 (c)(1),
(2), (4) Date: Jun. 3, 2011

(87) PCT Pub. No.: WO2010/063401
PCT Pub. Date: Jun. 10, 2010

(65) Prior Publication Data
US 2011/0245414 A1 Oct. 6, 2011

(30) Foreign Application Priority Data
Dec. 4, 2008 (EP) .................................... 08021050

(51) Int. Cl.
*C08F 2/30* (2006.01)
*C08F 120/18* (2006.01)
*C07C 69/54* (2006.01)

(52) U.S. Cl.
USPC ...... 524/807; 252/388; 252/389.23; 252/395; 252/396; 526/320; 526/328; 526/277; 526/287; 524/558

(58) Field of Classification Search
USPC ............. 252/388, 389.23, 395, 396; 526/320, 526/328, 277, 287; 524/558, 807
See application file for complete search history.

(56) References Cited

U.S. PATENT DOCUMENTS 7,812,106 B2 10/2010 Breuer et al.

FOREIGN PATENT DOCUMENTS

| DE | 10340081 | 3/2005 |
|---|---|---|
| JP | 2003-327609 | 11/2003 |
| JP | 2003-327893 | 11/2003 |
| JP | 2003-327895 | 11/2003 |

OTHER PUBLICATIONS

"Machine Translation of JP 2003-327609", Jun. 2, 2011, 20 pgs.
"Machine Translation of JP 2003-327893", Jun. 2, 2011, 14 pgs.
"Machine Translation of JP 2003-327895", Jun. 2, 2011, 35 pgs.
"PCT International Search Report for PCT/EP2009/008416", Apr. 14, 2010, 3 pgs.

*Primary Examiner* — Vu A Nguyen
(74) *Attorney, Agent, or Firm* — Servilla Whitney LLC

(57) ABSTRACT

The invention relates to a copolymerizable emulsifier comprising (meth)acrylic acid esters, selected from compounds of the general formula (1) and (II), where: A is an acrylic group having 3 to 40 carbon atoms, x and y independently of each other are a hydrogen group or a methyl group, B is hydrogen or a sulfate or phosphate group, and n a number in the range of 0 to 40. The invention further relates to methods of using said copolymerizable emulsifier in the emulsion polymerization of olefinically unsaturated monomers to prepare polymers.

5 Claims, No Drawings

COPOLYMERIZABLE (METH)ACRYLIC ACID ESTERS

CROSS-REFERENCE TO RELATED APPLICATIONS

This application is the National Stage entry of PCT/EP2009/008416, filed on Nov. 26, 2009, which claims priority to European Patent application number EP08021050 filed on Dec. 4, 2008, both of which are incorporated herein by reference in their entireties.

BACKGROUND

1. Field of the Invention

The invention lies within the polymer sector and relates to the use of olefinically unsaturated compounds of specific structure as emulsifiers in emulsion polymerization.

2. Background Information

Emulsion polymerization is a specific method of polymerization wherein olefinically unsaturated monomers of low solubility in water are emulsified in water by means of emulsifiers and polymerized using water-soluble initiators such as potassium peroxodisulfate or redox initiators for example. Anionic and/or nonionic surfactants are the key constituents here in that they ensure the process of emulsion polymerization via micelle construction in the aqueous solution.

Copolymerizable emulsifiers are in great demand in industry since they are wholly or partly incorporated in the growing polymer chain and thus reduce the migration of free emulsifier molecules in the end-use product for example. Copolymerizable emulsifiers occupy a position halfway between monomers and conventional emulsifiers. Their reactivity has to be tailored to the monomer system used and they must not have an adverse effect on the properties of the polymer formed. At the same time, they must not lose their emulsificative properties as a result of the presence of a reactive group. Owing to this combination of specific properties, novel copolymerizable emulsifiers are greatly sought after in industry.

German laid-open specification DE-A-10340081 describes copolymerizable surfactants of the formula $HOOC\text{---}CH\text{=}CH\text{---}COO\text{---}(BO)_z(PO)_y(EO)_xR^1$, where $R^1$ is an alkyl radical or alkylphenol radical having 8 to 24 carbon atoms, BO is a butylene oxide unit, PO is a propylene oxide unit and EO is an ethylene oxide unit, and the numbers x, y and z are each independently 0 or numbers from 1 to 50, with the proviso that at least one of x, y and z is other than 0, wherein the carboxyl group may be wholly or partly present in neutralized form and the C=C double bond may be cis- or trans-configured.

SUMMARY

The problem addressed by the present invention is that of providing compounds which, singly or admixed with other compounds, are useful as copolymerizable emulsifiers for emulsion polymerization.

Used as emulsifiers for emulsion polymerization, these should have the particular effect of minimizing coagulum. Furthermore, these copolymerizable emulsifiers should be pourable/pumpable in an aqueous offering.

Finally, the use as emulsifiers in emulsion polymerization should provide latices which, compared with latices obtained using comparable non-copolymerizable emulsifiers, have improved properties in respect of electrolyte stability, alkali resistance and/or viscosity.

The invention provides for the use of (meth)acrylic esters selected from compounds of the general formulae (I) and (II)

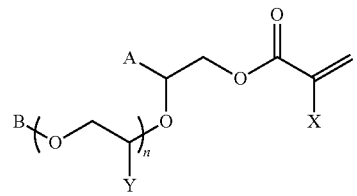
(I)

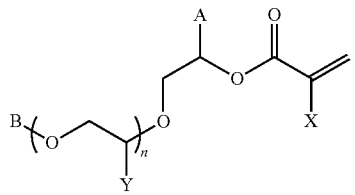
(II)

where
A is an alkyl radical of 3 to 40 carbon atoms,
X and Y are each independently hydrogen or a methyl radical,
B is hydrogen or a sulfate or phosphate group, and
n is a number in the range from 0 to 40,
as copolymerizable emulsifiers in the emulsion polymerization of olefinically unsaturated monomers.

DETAILED DESCRIPTION

The compounds (I) and (II) comprise the structural element

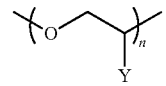

where, as mentioned, the definitions are as follows:
Y is hydrogen or a methyl radical
n is a number in the range from 0 to 40.

It may be emphasized that the formula notation used is intended to express the fact that the recited structural element derives from ethylene oxide (EO) or propylene oxide (PO) in the event that—logically in the case where the index n is other than zero—this unit results synthetically from an addition reaction of EO or PO, or ethylene glycol or propylene glycol (for n=1), or polyaddition reaction of EO and/or PO, or polyethylene glycol or polypropylene glycol, or corresponding mixed EO-PO copolymers (for n≥2). It may further be expressly emphasized that this structural element may be constructed both exclusively of EO units and exclusively of PO units, or else may comprise EO units and PO units in mixed form, distributed randomly or in blocks. Therefore, the formulaic representation used for the recited structural element represents an abbreviated notation for the recited possibilities mentioned, which are self-evident to a person skilled in the art.

For instance, Y=H and n=5 is to be understood as meaning that the structural element contains five interlinked EO units, corresponding to a $\text{---}(O\text{---}CH_2\text{---}CH_2\text{---})_5\text{---}$ grouping; whereas Y=$CH_3$ and n=5 is to be understood as meaning that the structural element contains five interlinked PO units, corresponding to a $\text{---}(O\text{---}CH_2\text{---}CH(CH_3))_5\text{---}$ grouping, although, as a person skilled in the art will know, the orientation of the methyl group within the structural element can be realized for each PO unit in two ways, namely as —(O—CH$_2$—CH(CH$_3$))— or —(O—CH(CH$_3$)—CH$_2$)—.

The Compounds (I) and (II)

The alkyl radical A comprises linear or branched, saturated or unsaturated alkyl groups having 3 to 40, preferably 10 to 20 and more preferably 12 to 18 carbon atoms. Very particular preference is given to the following alkyl radicals A: lauryl (C12), myristyl (C14), cetyl (C16), stearyl (C18), oleyl (olefinically unsaturated C18) and isotridecyl.

The compounds of formulae (I) and (II) according to the present invention are formally esterification products of acrylic acid and/or methyl acrylic acid.

The degree of alkoxylation n in the present invention is in the range from 0 to 40, preferably in the range from 1 to 20 and more preferably in the range from 2 to 10.

The B group is hydrogen or a sulfate or phosphate group.

In one embodiment, B is a sulfate or phosphate group. It is preferable in this case that the sulfate or phosphate group B is present in neutralized form. The sulfate or phosphate group may be neutralized with, for example, alkali or alkaline earth metal hydroxides such as sodium hydroxide, potassium hydroxide, calcium hydroxide or magnesium hydroxide or amines such as ammonia or ethanolamines. The salt form of compounds (I) and (II) is notable for good solubility in water.

In one embodiment, B is hydrogen. The compounds (I) and (II) then are nonionic and particularly but not exclusively useful for improving the stabilization of the latices against ionic influences.

The compounds of formulae (I) and (II) are for example obtainable by epoxidizing commercially available alpha-olefins by means of formic acid and hydrogen peroxide, then opening the epoxide ring of the resultant intermediate 1 by means of acrylic acid or methacrylic acid, optionally alkoxylating the OH group of the resultant intermediate 2 by reaction with ethylene oxide and/or propylene oxide, and finally, if desired, sulfating or phosphating the terminal OH group. Logically, the last step is optional or obligatory in respect of the meaning of the B group: when B is hydrogen, this step is omitted; when B is a sulfate or phosphate group, this step is carried out.

Since intermediate 1 in the synthesis described reacts with acrylic or methacrylic acid by opening the oxirane ring, this reaction generally results in mixtures of compounds (I) and (II) being obtained.

Use of Compounds (I) and (II)

Compounds (I) and (II) to be used according to the present invention polymerize readily and completely together with other olefinically unsaturated monomers different therefrom while promoting the formation of a foam-free and homogeneous emulsion.

When B is a sulfate or phosphate group, the compounds (I) and (II) are preferably used in an emulsion polymerization in partly or wholly neutralized form ("salt form" of the sulfate or phosphate group). This partly or wholly neutralized form is readily obtainable by partly or wholly neutralizing the compounds (I) in a conventional manner, for example using alkali or alkaline earth metal hydroxides such as sodium hydroxide, potassium hydroxide, calcium hydroxide or magnesium hydroxide or using amines such as ammonia or ethanolamines. The salt form of compounds (I) and (II) is notable for good solubility in water.

Process for Producing Polymers

The present invention further provides a process for preparing polymers by emulsion polymerization of olefinically unsaturated monomers, which comprises utilizing the compounds (I) and (II) mentioned above as copolymerizable emulsifiers.

The present invention process using compounds (I) and (II), particularly in salt form when B is a sulfate or phosphate group, provides polymers having special shear and electrolyte stability and also a low coagulum content.

One embodiment of the invention provides latices which in turn are additionally notable for special resistance to water and also stability to temperature fluctuations and which do not give rise to any discernible migration of the emulsifier into the film.

There is a further advantage to the process of the present invention in that it is virtually foam-free and reliably avoids the formation of volatile organic compounds. Since incorporation of emulsifier (I) and (II) in the polymer is virtually quantitative, the use thereof also does not present any biodegradability issues. The olefinically unsaturated esters (I) and (II) are further virtually devoid of any tendency to homopolymerize.

It was found that the use of compounds (I) and/or (II) as emulsifiers in emulsion polymerization provides latices having improved properties in respect of electrolyte stability, alkali resistance or viscosity, compared with such latices obtained with comparable non-copolymerizable emulsifiers (cf. examples 1 and 2 and also table 1). The examples in the example part illustrate the positive properties of the compounds to be used according to the present invention. Combinations of (I) and/or (II) with typical surfactants of the nonionic or anionic type can also be used, and likewise exhibit a positive profile of properties.

The latices of the present invention can be used in the coatings industry for example. It was found that coatings obtained using the latices of the present invention possess higher corrosion protection than conventional coatings. This is shown in examples 5 and 6 (comparative example).

Monomers

The olefinically unsaturated esters of the general formulae (I) and (II) to be used according to the present invention are useful as emulsifiers in the emulsion polymerization of virtually all industrially important, substantially water-insoluble monomers, but preferably (meth)acrylic, styrenic and vinylic compounds.

Typical examples of these monomers are vinylaromatics, e.g., styrene, divinylbenzene or vinyltoluene, polymerizable olefins and diolefins such as propene, butadiene or isoprene, esters of acrylic or methacrylic acid with linear or branched alcohols having 1 to 18 carbon atoms, more particularly of alcohols having 1 to 8 carbon atoms and—particularly preferably—of methyl esters, ethyl esters and butyl esters thereof, vinyl esters of acids having 2 to 12 carbon atoms, more particularly vinyl acetate, vinyl propionate, vinyl 2-ethylhexanoate and vinyl laurate, vinyl alkyl ethers having alkyl groups of 1 to 8 carbon atoms, vinyl chloride, vinylidene chloride and the like.

Monomers selected from the group of alkyl acrylates, styrene acrylates, VeoVa compounds or mixtures thereof, with or without addition of acrylic acid or methacrylic acid, are particularly preferred in the context of the present invention.

In the presence of the copolymerizable emulsifiers (I) to be used according to the present invention, the monomers can be homopolymerized or they can be copolymerized with others of the recited compounds from the above listing. It is further possible to perform copolymerizations involving up to 50% by weight of further inherently partly or wholly water-soluble monomers other than the compounds (I) and (II) according to the present invention, examples being acrylonitrile, methacrylonitrile, monoesters of maleic and/or fumaric acid with 1 to 8 carbon atoms, acrylic acid, methacrylic acid, maleic acid, fumaric acid, crotonic acid and/or itaconic acid.

In one embodiment, monomers used in the process of the present invention are combinations of styrene/butyl acrylate, vinyl acetate/butyl acrylate or styrene/butadiene.

Co-Emulsifiers

It is further also possible for the compounds (I) and (II) which are to be used according to the present invention to be used in combination with known nonionic and/or anionic co-emulsifiers. This can lead to dispersions of enhanced stability, for example in respect of shearing forces, temperature effects and electrolytes. The co-emulsifiers are added in amounts of 0.5% to 5% and preferably 1% to 3% by weight, based on total monomers used. The co-emulsifiers may be initially charged at the start of the polymerization together with the emulsifiers, or may be added in the course of the polymerization. In a further version, a pre-emulsion is prepared using or co-using the co-emulsifiers and added in the course of the polymerization. It is also possible for the dispersions obtained using the acrylic and/or methacrylic esters of the present invention to be admixed with co-emulsifiers for post-stabilization.

The compounds (I) and (II) to be used according to the present invention can also be used together with protective colloids. Typical examples of protective colloids of this type are fully or partially hydrolyzed homo- and/or copolymers of vinyl acetate, e.g., partially hydrolyzed polyvinyl acetate, or fully hydrolyzed copolymers of vinyl acetate and vinyl ethers. Preferred copolymers have from 1 to 4 carbon atoms in the ether moiety of the polyvinyl ether. Further protective colloids may be derived from polysaccharides. Especially cellulose ethers such as hydroxyethylcellulose, hydroxypropylcellulose, carboxymethylcellulose, methylcellulose, ethylcellulose or cellulose mixed ethers are suitable. Polyacrylamide and its copolymers with acrylic acid, acrylonitrile or acrylic esters are also suitable. It is similarly possible to use condensation products of naphthalenesulfonic acid and formaldehyde or other water-soluble formaldehyde resins, particularly urea-formaldehyde resins. Finally casein, gelatin, gum arabic and also natural starch and substituted derivatives of starch such as hydroxyethyl starch are suitable protective colloids.

Emulsion Polymerization

One embodiment utilizes the emulsifiers (I) and (II) in emulsion polymerization in amounts from 0.1% to 25% by weight, based on the sum total of the monomers.

The aqueous dispersions typically to be prepared in the first step of the process using compounds (I) and (II) include in practice from 15% to 75% by weight of polymerized monomers (dry residue) in water or a mixture of water and water-soluble organic solvents. The range from 20% to 60% by weight of dry residue is preferred; however, aqueous dispersions with less than 15% by weight of dry residue are also obtainable for special applications. The aforementioned processes of emulsion polymerization may also utilize further customary polymerization aids, more particularly initiators, for example inorganic peroxide compounds such as potassium persulfate or ammonium persulfate or hydrogen peroxide, organic peroxide compounds or organic azo compounds, where these can be used for emulsion polymerization. Initiators are used in customary amounts, i.e., from 0.05% to 2% by weight and preferably from 0.1% to 0.5% by weight. Suitable aids further include buffer substances, e.g., sodium bicarbonate, sodium pyrophosphate or sodium acetate, which can each be used in amounts of up to 2% by weight. Accelerants such as formaldehydesulfoxylate can also be used. It is further possible to use customary molecular weight regulators used in emulsion polymerization, e.g., butenol or else organic thio compounds such as mercaptoethanol, thioglycolic acid, octyl mercaptan or tert-dodecyl mercaptan. To perform the polymerization processes various methods typically employed in emulsion polymerization are possible, for example a total initial charge of all the reactants, a monomer feed or an emulsion feed. In general, the temperature of the polymerization medium is maintained for this purpose in a range from 40 to 100 and more particularly from 50 to 90° C. The pH is advantageously maintained in a range between 3 and 9, although the compounds of the present invention also tolerate an emulsion polymerization at lower pH values. The aforementioned possible versions of the emulsion polymerization process are advantageously carried out in coolable and heatable containers equipped with stirrers and temperature measurement equipment, for example stirred pressure tanks. It is similarly possible to use coiled-tube reactors or so-called loop reactors. After the polymerization has ended, the polymer dispersion is advantageously cooled down and removed from the reactor via screening means. When the reaction products are to be isolated as solid products, the polymer dispersion is advantageously precipitated or spray dried. Preferably, however, the as-polymerized dispersions are used directly as binders for paints, adhesives, papercoating slips or other coating materials. Further conditions for emulsion polymerization processes using the (meth)acrylic esters of the general formulae (I) and (II) which are to be used according to the present invention can be freely chosen or adapted to the particular requirements in a conventional manner by a person skilled in the art.

EXAMPLES

Emulsifiers Used

C12-epoxyacryloyl-10EO Phosphate:

This is a compound in accordance with the present invention. It was obtained as follows:

1,2-Dodecene was epoxidized in a conventional manner to form the intermediate 1.

Then, 1304.16 g (6.7 mol) of this intermediate 1 were heated to 60° C. and admixed with 3.57 g of 4-methoxyphenol. Then, a mixture of 482.08 g (6.7 mol) of acrylic acid and 17.86 g of triphenylphosphine was metered in, while the temperature of the reaction mixture was raised in the meantime from 60° C. to 90° C. On completion of the metered addition the reaction was allowed to proceed at 90° C. until the acid number of the reaction mixture was below 3 mg KOH/g (intermediate 2). 400 g (1.5 mol) of intermediate 2 were admixed with 264.30 g (6 mol) of ethylene oxide, 2 g of aqueous potassium hydroxide solution (50%) and 0.13 g of phenothiazine and purged with nitrogen. This was followed by ethoxylation at 150 to 155° C. and 4.5 bar pressure to form intermediate 3.

41.44 g (0.29 mol) of phosphorus pentoxide were metered a little at a time into 258.56 g (0.58 mol) of intermediate 3 in the course of an hour under vigorous stirring. All the while care was taken to ensure that the reaction temperature does not rise above 60° C. On completion of the metered addition the reaction was continued at 90° C. for a further 2 hours to form the end product.

Disponil FEP 5600:

This is a commercial fatty alcohol ether phosphate available from Cognis.

C12-Epoxyacryloyl-10EO

This emulsifier according to the present invention was synthesized as per the abovementioned C12-epoxyacryloyl-10EO phosphate, except that the synthesis was discontinued after the ethoxylation.

Disponil FEP 5600:

This is a commercial fatty alcohol ether phosphate available from Cognis.

Test Methods Used

The emulsions prepared were characterized using the following parameters:

The dry residue was determined as follows: 5 grams of the emulsion were introduced into a Satorius 709301 dry residue apparatus, and dried to constant weight. The result is reported in percent by weight dry residue. This is the meaning of the data in the tables below.

The viscosity of the emulsions prepared was determined by the Brookfield method at 20 rpm, using spindle 1, the emulsions being employed as they were. The figures for the viscosity in the tables below are given with mPas as the unit.

The pH of the emulsions prepared was determined electrochemically in accordance with DIN 19268, using a pH electrode.

The average particle diameter of the emulsions prepared was determined by means of a Coulter Nano-Sizer. The figures for the particle diameter in the tables below are reported with nm (nanometers) as the unit.

The total coagulum content of the emulsions prepared was determined gravimetrically after filtration through an 80 micrometer filter (wet coagulum).

The coagulum content thus determined is reported as % coagulum based on the solids content of the emulsion. The solids content of the emulsion here means the amount of monomers employed.

The coagulum content is an important variable to the skilled person for assessing the quality of an emulsion prepared by emulsion polymerization.

The electrolyte stability of the emulsions prepared is determined by treating samples of this emulsion (10 g) each with 10 ml of 6 different electrolyte solutions and checking for formation of coagulum. The electrolyte solutions are 1% and 10% solutions of each of NaCl, $CaCl_2$, and $AlCl_3$. The datum reported is the strongest electrolyte solution for which there is still no formation of coagulum.

The freeze/thaw stability of the emulsions obtained is determined by cooling a sample of the emulsion from 23° C. down to −5° C. in the course of 16 hours, and on reaching the latter temperature warming it back up again to 23° C. in the course of 8 hours. After this, the emulsion is visually inspected for homogeneity. This cycle is repeated a total of five times, the minimum temperature in each cycle being lowered by a further 5° C., i.e., the sample is cooled down to −10° C. in the second cycle, down to −15° C. in the third cycle, etc.

Production of Latices

Example 1

Test

A reactor vessel was charged with 260.37 g of distilled water, 1.75 g of C12-epoxyacryloyl-10EO phosphate, 0.47 g of potassium peroxodisulfate and 40 g of a pre-emulsion of 213.0 g of VeoVa 10, 151.5 g of methyl methacrylate, 94.7 g of butyl acrylate, 14.2 g of acrylic acid, 1.75 g of C12-epoxyacryloyl-10EO phosphate, 1.89 g of potassium peroxodisulfate and 260.37 g of distilled water. The reactor was heated up to 80° C. After the start of the polymerization the remaining pre-emulsion was metered in at a uniform rate over 3 hours. On completion of the addition the batch was post-polymerized for 1 hour.

Example 2

Comparative

Example 1 was repeated except that the C12-epoxyacryloyl-10EO phosphate was replaced by the same amount of Disponil FEP 5600.

Test Results

The latices obtained were more particularly characterized. The results are shown in table 1.

TABLE 1

|  | Latex of Example 1 | Latex of Example 2 |
| --- | --- | --- |
| Particle size [nm] | 182 | 116 |
| Viscosity (20° C.) [mPas] | 135 | 1225 |
| Electrolyte stability | 10% CaC12 | 1% CaC12 |

Example 3

Test

The emulsion of example 1 was cooled from 23° C. down to −5° C. in the course of 16 hours and on reaching the latter temperature warmed up again to 23° C. in the course of 8 hours. After this the emulsion was visually inspected for homogeneity. This cycle was repeated a total of five times, the minimum temperature in each cycle being lowered by a further 5° C., i.e., the emulsion was cooled down to −10° C. in the second cycle, down to −15° C. in the third cycle, etc.

The invention emulsion of example 1 was still homogeneous, i.e., an intact emulsion, after five cycles.

Example 4

Comparative

The process of example 3 was repeated with the emulsion of example 2. It was found that the emulsion exhibited phase separation after just the first cycle. The coagulum formed was not redispersible.

What is claimed is:

1. A method of corrosion protection, the method comprising:
providing a copolymerizable emulsifier that comprises a (meth)acrylic ester selected from compounds of the general formula (II)

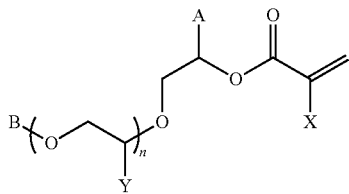

wherein
A is an alkyl radical of 3 to 40 carbon atoms,
X and Y are each independently hydrogen or a methyl radical,
B is hydrogen or a sulfate or phosphate group, and
n is a number in the range from 0 to 40;
forming a latex comprising polymers obtained by emulsion polymerization of olefinically unsaturated monomers with the copolymerizable emulsifier; and
using the latex for corrosion protection of a coating.

2. The method of claim 1 wherein B is hydrogen.

3. The method of claim 1 wherein B is a sulfate or phosphate group.

4. The method of claim 1 wherein the sulfate or phosphate group B is present in neutralized form.

5. The method of claim 1 wherein n is a number in the range from 1 to 20.

* * * * *

UNITED STATES PATENT AND TRADEMARK OFFICE
CERTIFICATE OF CORRECTION

PATENT NO. : 8,642,698 B2
APPLICATION NO. : 13/132638
DATED : February 4, 2014
INVENTOR(S) : Ronald Klagge et al.

It is certified that error appears in the above-identified patent and that said Letters Patent is hereby corrected as shown below:

On the title page item (73), "Duesseldolf" changed to --Duesseldorf--.

Signed and Sealed this
Twentieth Day of May, 2014

Michelle K. Lee
*Deputy Director of the United States Patent and Trademark Office*